United States Patent [19]

Holla et al.

[11] Patent Number: 5,554,788
[45] Date of Patent: Sep. 10, 1996

[54] PROCESS FOR THE STEREOSELECTIVE SYNTHESIS OF 3-SUBSTITUTED 2-THIOMETHYLPROPIONIC ACIDS

[75] Inventors: Wolfgang Holla, Kriftel; Bernhard Kammermeier; Gerhard Beck, both of Frankfurt, all of Germany

[73] Assignee: Hoechst Aktiengesellschaft, Frankfurt am Main, Germany

[21] Appl. No.: 411,831

[22] PCT Filed: Sep. 30, 1993

[86] PCT No.: PCT/EP93/02673

§ 371 Date: May 15, 1995

§ 102(e) Date: May 15, 1995

[87] PCT Pub. No.: WO94/00789

PCT Pub. Date: Apr. 14, 1994

[30] Foreign Application Priority Data

Oct. 1, 1992 [DE] Germany .......................... 42 33 099.8

[51] Int. Cl.$^6$ .................................................. C07C 315/02
[52] U.S. Cl. .............................................................. 562/429
[58] Field of Search ............................................... 562/429

[56] References Cited

FOREIGN PATENT DOCUMENTS

0309766A2  4/1989  European Pat. Off. .
0332008A2  9/1989  European Pat. Off. .

OTHER PUBLICATIONS

"Asymmetric Synthesis of the Enkephalinasa Inhibitor Thiorphan", David A. Evans et al., The Journal of Organic Chemistry, 50(11):1830–1835 (1985).

"Synthesis and Biological Activity of Some Transition–State Inhibitors of Human Renin", Peter Bühlmayer et al., Journal of Medicinal Chemistry, 31(9):1839–1846 (1988).

Primary Examiner—Joseph Conrad
Attorney, Agent, or Firm—Finnegan, Henderson, Farabow, Garrett & Dunner, L.L.P.

[57] ABSTRACT

Process for the stereoselective synthesis of 3-substituted 2-thiomethylpropionic acids Compounds of the formula I

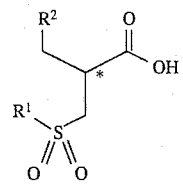

in which $R^1$ and $R^2$ are as defined can be prepared stereoselectively by reaction of acrylic acid or derivatives thereof or propionic acid or derivatives thereof with a chiral auxiliary, reaction with a mercaptan, stereoselective alkylation and subsequent hydrolysis and oxidation.

7 Claims, No Drawings

PROCESS FOR THE STEREOSELECTIVE SYNTHESIS OF 3-SUBSTITUTED 2-THIOMETHYLPROPIONIC ACIDS

This application is a 371 of PCT/EP93/02673 filed Sep. 30, 1993.

3-substituted 2-thiomethylpropionic acids and derivatives thereof, for example esters, are gaining interest as building blocks and as precursors for aspartyl protease inhibitors [P. Bühlmeyer et al., J. Med. Chem. 31 (1988), 1839; R. Henning, Nachr. Chem. Techn. Lab. 38 (1990), 460; J. R. Huff, J. Med. Chem. 34 (1991), 2305].

The compounds mentioned are already known. Moreover, a series of syntheses or processes for the preparation of these compounds has been described.

In this context, examples of some recent work include:
P. Bühlmeyer et al., J. Med. Chem. 31 (1988), 1839; K. Tsuji et al., Tetrahedron Lett. 30 (1989), 6189; M. Nakano et al., Tetrahedron Lett. 31 (1990), 1569; M. Nakano et al., Chem. Lett. (1990), 505; cf. also D. A. Evans et al., J. Org. Chem. 50 (1985), 1830.

The first-mentioned synthesis requires, inter alia, the use of formaldehyde and/or formaldehyde derivatives, which, like the by-products formed in this case, are regarded as being highly objectionable in terms of health because of their alkylating properties and necessitate specific safety measures which include the area of workplace health and safety [Merck Index 11, 4150].

Moreover, the preparation of optically pure compounds requires the splitting of a racemate. For this purpose the racemic acid is converted into the diastereomeric amides using L-phenylalaninol, these amides are separated by chromatography, and the desired isomer is obtained by hydrolysis of the corresponding amide. The large number of steps, the fundamental disadvantages of splitting a racemate and the scale-up problems involved in a chromatographic purification mean that this route appears unattractive for the preparation of relatively large quantities.

The synthesis according to Tsuyi et al. leads to optically pure material with a similar number of steps but without splitting a racemate. This synthesis comprises a number of steps for the introduction and elimination of protecting groups; some of the reagents employed are expensive, and in some cases carcinogenic formaldehyde derivatives are used or produced in the course of the syntheses [H. G. Neumann in "Allgemeine und spezielle Pharmakologie und Toxikologie" [General and Special Pharmacology and Toxicology], 4th edition, W. Forth, ed., B. I. Wissenschaftsverlag, Mannheim-Vienna-Zurich, p. 621 ff. (1983); Arch. Environ. Health 30 (2), 61]. Therefore, this synthesis route does not constitute an economically and ecologically justifiable alternative for the preparation of large quantities.

The preparation of 2-mercaptomethyldihydrocinnamic acid, which is shown in the context of the synthesis of thiorphan described by Evans and Mathre, is short in comparison with the two syntheses which have already been discussed, proceeds with a good overall yield, and enables the specific preparation of both enantiomers in high optical purity. The weak point in this synthesis is the complex introduction of the mercaptan grouping and the consequent necessity to use benzylthiomethyl bromide, which is objectionable in terms of health and is prepared from trioxane (as formaldehyde source), benzyl mercaptan (or benzylthiomethyl chloride) and HBr [H. G. Neumann in "Allgemeine und spezielle Pharmakologie und Toxikologie" [General and Special Pharmacology and Toxicology], 4th edition, W. Forth, ed., B. I. Wissenschaftsverlag, Mannheim-Vienna-Zurich, p. 621 ff. (1983); Arch. Environ. Health 30 (2), 61].

Nakano et al. describe two routes for the synthesis of the carbon framework of the compounds I. The first synthesis starts from diethyl malonate, and requires six steps and, in addition, chromatographic resolution of the diastereomers.

The second route proceeds via a chiral, non-racemic arylpropionyloxazolidinone and its stereoselective alkylation using benzyl bromomethyl ether [M. W. Holladay et al., J. Med. Chem. 30 (1987), 374] followed by chromatography. After removal of the benzyl group by hydrogenation, as in the case of the first route, the sulfur substituent is introduced by tosylation of the free hydroxyl group followed by substitution by $NaSCH_2CH_3$ in DMF.

These two synthesis routes are also characterized by: a high number of steps, carcinogenic and toxic formaldehyde derivatives as precursors or reagents, the complex introduction of the sulfur substituent, which is a process which is not entirely free from racemization, and, last but not least, the chromatographic separation of impurities and resolution of diastereomeric compounds.

The object on which the present invention is based is to develop a process for the synthesis of compounds of the formula I which has a low number of steps, does not require protecting group chemistry, does not require column chromatography steps, is stereoselective and leads selectively to the enantiomeric compounds of the formula I, does not require splitting of racemates or resolution of diastereomers, and represents an improvement, or is unobjectionable, from the points of view of health, ecology and safety.

This object is achieved by the process according to the invention. The subject of the invention is consequently a process for the stereoselective preparation of a compound of the formula I

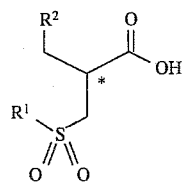

in which $R^1$ is $C_1$–$C_6$-alkyl, $C_3$–$C_6$-cycloalkyl, ($C_6$–$C_{12}$)-aryl-($C_1$–$C_4$)-alkyl or $C_6$–$C_{12}$-aryl or -heteroaryl or -heterocycloalkyl which may be substituted by 1, 2 or 3 identical or different hydroxyl, methoxy or trialkylsilyloxy groups; and $R^2$ is $C_6$–$C_{12}$-aryl which may be substituted by 1, 2 or 3 identical or different methoxy, halogen, cyano, methyl, trifluoromethyl, isopropyl or nitro groups;

is $C_3$–$C_9$-heteroaryl which may be substituted by 1, 2 or 3 identical or different methoxy, halogen, cyano, methyl, trifluoromethyl, isopropyl or nitro groups; or is $C_1$–$C_{10}$-alkyl, alkenyl or alkynyl which may be substituted by 1, 2 or 3 identical or different methoxy, halogen, cyano, methyl, trifluoromethyl, isopropyl or nitro groups and the compounds of the formula I may be present in the R or S form, which comprises converting a compound of the formula IIa or IIb or IIIa or IIIb, respectively, (chiral auxiliary), in which Y is =O or S,

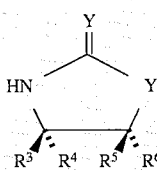

| | |
|---|---|
| $R^3=C_1-C_4\text{-alkyl}, R^5=C_6-C_{10}\text{aryl}, R^4=R^6=H,$ | IIa |
| $R^4=C_1-C_4\text{-alkyl}, R^6=C_6-C_{10}\text{aryl}, R^3=R^5=H,$ | IIb |
| $R^3=C_1-C_4\text{-alkyl}, C_1-C_2\text{-alkyl-}C_6-C_{12}\text{-aryl}, R^4=R^5=R^6=H,$ | IIIa |
| $R^4=C_1-C_4\text{-alkyl}, C_1-C_2\text{-alkyl-}C_6-C_{12}\text{-aryl}, R^3=R^5=R^6=H,$ | IIIb |

$a_1$) with acrylic acid or with derivatives of acrylic acid, into a compound of the formula IVa or IVb or Va or Vb, respectively, in which Y is =O or S,

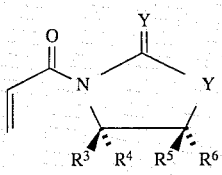

| | |
|---|---|
| $R^3=C_1-C_4\text{-alkyl}, R^5=C_6-C_{10}\text{-aryl}, R^4=R^6=H,$ | IVa |
| $R^4=C_1-C_4\text{-alkyl}, R^6=C_6-C_{10}\text{-aryl}, R^3=R^5=H,$ | IVb |
| $R^3=C_1-C_4\text{-alkyl}, C_1-C_2\text{-alkyl-}C_6-C_{12}\text{-aryl}, R^4=R^5=R^6=H,$ | Va |
| $R^4=C_1-C_4\text{-alkyl}, C_1-C_2\text{-alkyl-}C_6-C_2\text{-aryl}, R^3=R^5=R^6=H,$ | Vb | or $a_2$) with propionic acid or propionic acid derivatives which are in turn substituted in position $C_3$ by a radical X=Cl, Br, OTs, OMs, into a compound of the formula VIa or VIb or VIIa or VIIb, respectively, in which X and Y are as defined above,

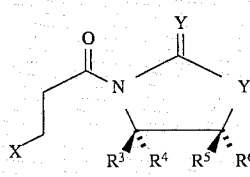

| | |
|---|---|
| $R^3=C_1-C_4\text{-alkyl}, R^5=C_6-C_{10}\text{-aryl}, R^4=R^6=H,$ | VIa |
| $R^4=C_1-C_4\text{-alkyl}, R^6=C_6-C_{10}\text{-aryl}, R^3=R^5=H,$ | VIb |
| $R^3=C_1-C_4\text{-alkyl}, C_1-C_2\text{-alkyl-}C_6-C_{12}\text{-aryl}, R^4=R^5=R^6=H,$ | VIIa |
| $R^4=C_1-C_4\text{-alkyl}, C_1-C_2\text{-alkyl-}C_6-C_{12}\text{-aryl}, R^3=R^5=R^6=H,$ | VIIb | b) reacting the compound of the formula IVa, IVb, Va, Vb, VIa, VIb, VIIa or VIIb obtained according to $a_1$) or $a_2$), directly or after isolation in a nonaqueous medium or in the presence of phase-transfer catalysts in aqueous two-phase systems, with a mercaptan of the formula $R^1SH$, in which $R^1$ is as defined above, into the corresponding compound of the formula VIIIa or VIIIb or IXa or IXb, respectively, in which $R^1$ and Y are as defined above,

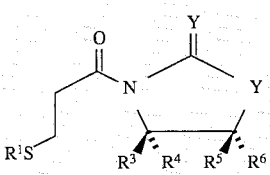

| | |
|---|---|
| $R^3=C_1-C_4\text{-alkyl}, R^5=C_6-C_{10}\text{-aryl}, R^4=R^6=H,$ | VIIIa |
| $R^4=C_1-C_4\text{-alkyl}, R^6=C_6-C_{10}\text{-aryl}, R^3=R^5=H,$ | VIIIb |
| $R^3=C_1-C_4\text{-alkyl}, C_1-C_2\text{-alkyl-}C_6-C_{12}\text{-aryl}, R^4=R^5=R^6=H,$ | IXa |
| $R^4=C_1-C_4\text{-alkyl}, C_1-C_2\text{-alkyl-}C_6-C_{12}\text{-aryl}, R^3=R^5=R^6=H,$ | | or $a_3$) converting a compound of the formula IIa or IIb or IIIa or IIIb, respectively, in the presence of a quantity of base which is sufficient for the deprotonation of the oxazolidinone and of the mercaptan $R^1SH$, in which $R^1$ is as defined above, into a compound of the formula VIIIa or VIIIb or IXa or IXb, respectively, by reaction with acryloyl or propionyl halides or their respective mixed anhydrides and further reaction of the reaction product with the mercaptan in one step, c) then converting the compound obtained according to b) or $a_3$) into the corresponding compound of the formula Xa, Xb, XIa or XIb by stereoselective alkylation,

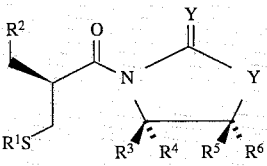

| | |
|---|---|
| $R^3=C_1-C_4\text{-alkyl}, R^4=R^6=H, R^5=C_6-C_{12}\text{-aryl},$ | Xa |
| $R^3=C_1-C_4\text{-alkyl}, C_1-C_2\text{-alkyl-}C_6-C_{12}\text{-aryl}, R^4=R^5=R^6=H,$ | XIa |

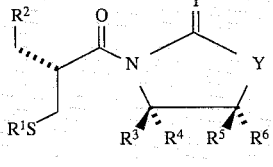

| | |
|---|---|
| $R^4=C_1-C_4\text{-alkyl}, R^6=C_6-C_{12}\text{-aryl}, R^3=R^5=H,$ | Xb |
| $R^4=C_1-C_4\text{-alkyl}, C_1-C_2\text{-alkyl-}C_6-C_{12}\text{-aryl}, R^3=R^5=R^6=H,$ | XIb | in which Y, $R^1$ and $R^2$ are as defined above, d) then converting the compound obtained in this way by reaction with $H_2O_2$ in alkaline solution, preferably with $LiOH/H_2O_2$, into compounds of the formula XII which may be present in the R or S form,

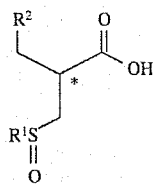

and
c) then converting the compound obtained in this way, by further oxidation, into the corresponding compound of the formula I.

The process according to the invention is particularly suitable for the preparation of compounds of the formula I in which $R^1$ is $C_1$–$C_4$-alkyl, $C_5$–$C_6$-cycloalkyl, $(C_6$–$C_{12})$-aryl-$(C_1$–$C_3)$-alkyl or $C_6$–$C_{12}$-aryl or -heteroaryl or -heterocycloalkyl which may be substituted by a hydroxyl, methoxy or trialkylsilyloxy group;

$R^2$ is $C_6$–$C_{12}$-aryl which may be substituted by a methoxy, halogen, methyl, trifluoromethyl or isopropyl group; is $C_3$–$C_6$-heteroaryl which may be substituted by a methoxy, halogen, methyl, trifluoromethyl or isopropyl group, or is $C_1$–$C_6$-alkyl, -alkenyl or -alkynyl.

Furthermore, the process according to the invention is particularly suitable for the preparation of compounds of the formula I in which $R^1$ is $C_1$–$C_4$-alkyl, $(C_6$–$C_{12})$-aryl-$(C_1$–$C_3)$-alkyl or $C_6$–$C_{12}$-aryl, and $R^2$ is $=C_6$–$C_{12}$-aryl, $C_3$–$C_6$-heteroaryl or $C_1$–$C_4$-alkyl, -alkenyl or -alkynyl.

The process according to the invention has very special importance for the preparation of compounds of the formula I in which $R^1$ is =tert-butyl and $R^2$ is =naphthyl.

The abovementioned substituent $C_6$–$C_{12}$-aryl is understood to be, for example, phenyl, naphthyl or biphenyl.

Alkyl, alkenyl and alkynyl may be straight-chain or branched.

Halogen is preferably fluorine, chlorine or bromine, particularly preferably chlorine.

Heterocycloalkyl or, respectively, heteroaryl comprises in particular compounds which contain up to 3, preferably and in particular 1 N, S and/or O atom in the ring. Examples which may be mentioned are pyridyl, furyl, pyrimidyl, pyrrolidino, pyrolyl, piperidino or piperidyl, especially pyridyl.

Compounds of the formulae IIa, IIb, IIIa and IIIb which are preferably used are those in which,

| | |
|---|---|
| $R^3$=Me, $R^5$=Ph, $R^4$=$R^6$=H | IIa |
| $R^4$=Me, $R^6$=Ph, $R^3$=$R^5$=H | IIb |
| $R^3$=CH(CH$_3$)$_2$, $R^4$=$R^5$=$R^6$=H | IIIa |
| $R^4$=CH(CH$_3$)$_2$, $R^3$=$R^5$=$R^6$=H | IIIb | and Y is =O.

Important intermediates in these synthesis routes are:
(4R,5S)- and (4S,5R)-4-methyl-5-phenyl-2-oxazolidinone,
(S)- and (R)-4-isopropyl-2-oxazolidinone
(4R,5S)- and (4S, 5R) -3-acryloyl-4-methyl-5-phenyl-2 -oxazolidinone,
(4S)- and (4R)-3-acryloyl-4-isopropyl-2-oxazolidinone,
(4R,5S)-3- and (4S,5R)-3-[1-oxo-3-halopropyl]-4-methyl-5- phenyl-2-oxazolidinone,
(4R,5S)-3- and (4S,5R)-3-[1-oxo-3-(alkyl- or arylsulfonyloxy)propyl] -4-methyl-5-phenyl-2-oxazolidinone,
(4S)- and (4R)-3-[1-oxo-3-halopropyl]-4-isopropyl-2-oxazolidinone,
(4S)- and (4R)-3-[1-oxo-3-(alkyl- or arylsulfonyloxy)propyl]-4-isopropyl-2-oxazolidinone,
(4R,5S)-3- and (4S,5R)-3-[1-oxo-2-(alkyl- or arylthio)methyl]propyl-4-methyl-5-phenyl-2-oxazolidinone,
(4S) and (4R)-3-[1-oxo-2-(alkyl- or arylthio)methyl]propyl-4-isopropyl-2-oxazolidinone,
(4R,5S)-3-[(2S)-1-oxo-2-(alkyl- or arylthiomethyl)-3-(alkyl- or aryl)propyl]-4-methyl-5-phenyl-2-oxazolidinone,
(4S,5R)-3-[(2R)-1-oxo-2-(alkyl- or arylthiomethyl)-3-(alkyl- or aryl)propyl]-4-methyl-5-phenyl-2-oxazolidinone
(4S)-3-[(2R)-1-oxo-2-(alkyl-or arylthiomethyl)-3-(alkyl- or aryl)propyl-4-isopropyl-2-oxazolidinone,
(4R)-3-[(S)-1-oxo-2-(alkyl- or arylthiomethyl)-3-(alkyl- or aryl)propyl]-4-isopropyl-2-oxazolidinone and
(2S)- and (2R)-2-(alkyl- or arylsulfoxymethyl)-3-(alkyl- or aryl)propionic acid.

The acryloyl compounds of the formulae IIa, IVb, Va or Vb and the propionyl compounds of the formulae VIa, rib, VIIa or VIIb can be obtained by complete, irreversible deprotonation of the compounds of the formulae IIa, IIb, IIIa or IIIb, which are readily accessible in good yields [D. A. Evans, D. J. Mathre, J. Org. Chem. 50 (1985), 1830; D. A. Evans, J. R. Gage, Org. Synth. 68 (1989), 77; P. G. M. Wuts, L. E. Pruitt, Synthesis 1989, 622], with sodium hydride, BuLi, KOtBu in anhydrous aprotic solvents such as tetrahydrofuran, dimethoxyethane, tert-butyl methyl ether, toluene, followed by reaction with the corresponding carboxylic acid halides, preferably the acid chlorides or the mixed anhydrides (prepared, for example, from acrylic or 3-chloro- or bromo-, propionic acid, triethylamine and carboxylic acid chlorides such as pivaloyl chloride) at low temperatures (–80° C. to –20° C.). It was possible to do without the stabilization with Cu/Cu$_2$Cl$_2$ in the case of the acryloyl compounds (see Binger et al., Liebigs Ann. Chem. 1989, 739; Oppolzer et al. Tetrahedron Lett. (1991), 4893).

The preferred procedure, especially for the synthesis of the acryloyl compounds, is reaction of the oxazolidinones at room temperature in tetrahydrofuran with sodium hydride, followed by cooling to from –80° C. to –60° C. and reaction with the acid chloride.

In order to carry out the conjugate mercaptan addition, the appropriate thio compounds are reacted, in solution in ether (preferably THF), with alkali metal hydrides (preferably NaH) or appropriate organometallic compounds (preferably BuLi) or with fluorides (e.g. tetra-n-butylammonium fluoride) and are then reacted with the compounds of the formulae IVa, IVb, Va or Vb.

As an alternative to this, the mercaptan addition can also be carried out with phase-transfer catalysis (e.g. with methyltrioctylammonium chloride or tetra-n-butylammonium hydrogen sulfate) in a mixture of aqueous NaOH and organic solvents such as methylene chloride, dichloroethane, tetrahydrofuran, dimethoxyethane, tert-butyl methyl ether, diisopropyl ether, etc.

A further possibility for the synthesis of the compounds VIIIa,b, IXa,b is the reaction of compounds of the formula VIa,b, VIIa,b with mercaptans of the formula $R^1$SH, in which $R^1$ is as defined above, in the presence of bases such as $K_2CO_3$ in protic solvents such as ethanol.

However, because of the higher overall yield, the nature of the by-products and the increased ease and rapidity of working up and isolating the products, "one-pot" variants have proven advantageous. Such variants lead, in accordance with the invention, in one step directly from compounds of the formulae IIa or IIb or IIIa or IIIb, respectively, to compounds of the formulae VIIIa or VIIIb and/or IXa or IXb, respectively. For this purpose the chiral auxiliaries of the formulae IIa or IIb or IIIa or IIIb, respectively, are reacted with a quantity of base (NaH, BuLi, etc.) which is sufficient both for the deprotonation of the oxazolidinones and for the mercaptan, acryloyl halide or propionyl halide or their respective mixed anhydride is added after complete deprotonation, and the respective mercaptan is added to the resulting mixture after acylation is complete (monitoring by TLC).

Furthermore, the following procedure is preferred: After completion of the NaH- or BuLi-mediated acylation of the compounds of the formulae IIa, IIb, IIIa or IIIb with acryloyl or propionyl halide or with the respective mixed anhydrides at from −80° C. to −60° C., proton donors such as, for example, acetic acid, citric acid, water are added, the mixture is heated to room temperature, a pH from 9 to 12 is established (for example using aqueous NaOH) and the mercaptan and a phase-transfer catalyst such as, for example, tetra-n-butylammonium hydrogen sulfate, methyltrioctylammonium chloride are added.

The alkylation of the compounds of the formulae VIIIa, VIIIb, IXa or IXb is preferably carried out in anhydrous aprotic solvents, preferably in THF, by stereoselective enolate formation (D. A. Evans, Pure Appl. Chem. 53 (1981) 1109; D. A. Evans, Aldrichimica Acta 15 (1982), 23) for example at from −80° C. to −60° C. using lithiated secondary a mines (e.g. LDA) or Na or Li hexamethyldisilazane (NaHMDS, LiHMDS) followed by reaction with alkyl or aryl halides, preferably at from −50° C. to −10° C.

The subsequent mild elimination of the chiral auxiliary is carried out using $H_2O_2$ in alkaline solution at from −10° to −30° C., preferably using $LiOH/H_2O_2$ at from 0° C. to 25° C., preferably in solvents such as dioxane, THF, dimethoxyethane or tBuOMe or aqueous mixtures of these solvents (Evans et al., Tetrahedron Lett. 28 (1987), 6141).

If desired, the compounds of the formula Xa, XIa, Xb, XIb can be converted into carboxylic acid derivatives such as esters and amides, or into alcohols, by transesterification (for example with LiOR, $Ti(OR)_4$ or BrMgOR), by transamination (for example with $Me_2AlN(OR)R$) or by reduction, for example with $LiAlH_4$, $LiBH_4$. In this context R is Me, Et, $CH_2Ph$, isopropyl or n-butyl.

In the case of the $LiOH/H_2O_2$-induced hydrolysis of the compounds of the formulae Xa, Xb, XIa or XIb this leads, as planned, directly to the sulfoxides of the formula XII. The oxidation to give the compounds of the formulae I is possible both directly and also after prior isolation of the sulfoxides.

Suitable oxidizing agents are:

metachloroperbenzoic acid (mCPBA), for example in $CH_2Cl_2$ at 0°–25° C.;

potassium permanganate ($KMnO_4$), for example in $H_2O/K_2CO_3$ at room temperature;

Oxone ($2KHSO_5.KHSO_4.K_2SO_4$) in water at room temperature;

magnesium monoperoxyphthalate (MMPP) in water at room temperature;

particularly preferred is $H_2O_2$, 30% strength, at room temperature in $CH_2Cl_2$, in the presence of acetic acid and polyphophoric acid.

A great advantage in process terms, especially for large batches, results from the combination of alkylation, hydrolysis and oxidation into a one-pot process.

Following direct conversion of the compounds of the formulae VIIIa, VIIIb, IXa or IXb into compounds of the formulae XII or I, the separation of the unwanted byproducts and the removal of the excess reagent is limited to a simple extractive working-up of the basified reaction mixture (e.g. partition between water and methylene chloride). After acidification of the aqueous phase and extraction with ethyl acetate, the desired compounds of the formulae XII or I are obtained in high chemical and optical purity.

The process according to the invention therefore comprises a sequence of not more than 4 steps with yields of 60–95% (the overall yield is between 30 and 40%). The working up of the intermediates and end products does not require column chromatography but is limited to crystallization, extraction and filtration. The starting compounds used are inexpensive and represent no problems from the working and safety point of view.

| List of abbreviations | |
|---|---|
| Bu | butyl |
| LDA | lithium diisopropylamide |
| Me | methyl |
| OTs | p-toluenesulfonyl |
| OMs | methylsulfonyl |
| Ph | phenyl |
| t | tertiary |
| THF | tetrahydrofuran |

The examples which follow are intended to illustrate the invention in more detail:

EXAMPLE 1

Synthesis of Compound IVa Where $R^3$=methyl, $R^5$=Phenyl 1.8 g (45 mmol) of NaH (60% pure) are placed in 50 ml of THF, and 5 g (28 mmol) of the oxazolidinone of the formula IIa where $R^3$=Me, $R^5$=Ph in 20 ml of THF are added at from 20° to 25° C. The mixture is stirred for one hour at from 20° to 25° C. and then cooled to −70° C., and 4.7 ml (58 mmol) of acryloyl chloride are added dropwise. The temperature is maintained at between −60° and −65° C. After stirring for 10 minutes the reaction has ended. 50 ml of saturated $NaHCO_3$ solution are added dropwise. During this addition the temperature rises to about −10° C. The cooling bath is then removed, ethyl acetate is added, the phases are separated, the organic phase is washed twice with saturated NaCl solution and dried with $Na_2SO_4$ and the solvent is distilled off in vacuo. The residue is taken up in tert-butyl methyl ether and the precipitate is separated off. The solution which remains (filtrate) contains 4.6 g (69%) of the desired product.

$^1$H-NMR (200 MHz, $CDCl_3$): σ=0.95 (d; 3H, CHCH$H_3$); 4.82 (quint; 1H, CHC$H$CH$_3$); 5.70 (d; 1H, CHC$H$Ph); 5.92 (dd; 1H, olef.); 6.57 (dd; 1H, olef.); 7.1–7.5 (m; 5H, Ph); 7.53 (dd; 1H, olef.).

EXAMPLE 2

Synthesis of Compound VIIIa Where $R^1$=C(CH$_3$)$_3$, $R^3$=Methyl, $R^5$=Phenyl 10 ml of toluene, 5 ml of water, 1 ml of 5N NaOH, 20 mg of tetra-n-butylammonium hydrogen sulfate and 0.76 ml (6.74 mmol) of tert-butyl mercaptan are added to 1.39 g (6.0 mmol) of the compound IVa where $R^3$=Me, $R^5$=Ph, and the mixture is stirred at room temperature for 2 h. Following the addition of 100 ml of water, the mixture is extracted with 100 ml of ethyl acetate, the organic phase is dried with MgSO$_4$ and concentrated on a rotary evaporator in vacuo, and the residue is treated with tert-butyl methyl ether. The precipitate which forms is filtered off and discarded, and the solution which remains is concentrated to give 1.54 g (80%) of the mercapto compound of the formula VIIIa where R$^1$=t-Bu, R$^3$=Me, R$^5$=Ph.

$^1$H-NMR (200 MHz, CDCl$_3$): σ=0.92 (d; 3H, CHC$\underline{H}_3$); 1.35 (s; 9H, C(CH$_3$)$_3$); 2.8–2.9 (m; 2H, CH$_2$CH$_2$); 3.2–3.3 (m; 2H, CH$_2$CH$_2$); 4.78 (quint; 1H, CHC$\underline{H}$CH$_3$); 5.68 (d; 1H, CHC$\underline{H}$Ph); 7.25–7.50 (m; 5H, Ph). m.p.: 65°–67° C.

EXAMPLE 3

Synthesis of Compound VIIIa Where R$^1$=C(CH$_3$)$_3$, R$^3$=Me, R$^5$=Ph 0.7 g (3.0 mmol) of the compound IVa where R$^3$=Me, R$^5$=Ph, 0.012 g (0.3 mmol) of NaOH in 0.5 ml of water, 10.5 mg of tetra-n-butylammonium hydrogen sulfate and 0.39 ml (3.4 mmol) of tert-BuSH are stirred, in a procedure similar to Example 2, in 4–5 ml of methylene chloride for 2 h at room temperature. Working up (extraction with CH$_2$Cl$_2$, drying with MgSO$_4$) as in Example 2 gives 723 mg (75%) of the compound VIIIa where R$^3$=Me, R$^5$=Ph.

$^1$H-NMR (200 MHz, CDCl$_3$): σ=0.92 (d; 3H, CHC$\underline{H}_3$); 1.35 (s; 9H, C(CH$_3$)$_3$); 2.8–2.9 (m; 2H, CH$_2$CH$_2$); 3.2–3.3 (m; 2H, CH$_2$CH$_2$); 4.78 (quint; 1H, CHC$\underline{H}$CH$_3$); 5.68 (d; 1H, CHC$\underline{H}$Ph); 7.25–7.50 (m; 5H, Ph). m.p.: 65°–68° C.

EXAMPLE 4

Synthesis of Compound VIIIb Where R$^1$=C(CH$_3$)$_3$, R$^4$=Me, R$^6$=Ph 7.2 g (about 180 mmol) of NaH (55–60% pure) are placed in a 1 liter 4-necked flask with 200 ml of dry tetrahydrofuran. A mixture of 20 g (112.8 mmol) of the oxazolidinone of the formula IIb where R$^4$=Me, R$^6$=Ph and 80 ml of dry THF is added dropwise thereto at room temperature. The reaction mixture is stirred for one hour at room temperature and then cooled to from –60° to –65° C., and 11.8 ml (146.64 mmol) of acryloyl chloride are then slowly added. After stirring for 10 minutes the cooling bath is removed and 120 ml of water are slowly added. A pH of from 11 to 12 is then established with 5N NaOH. When the pH remains constant, 450 to 500 mg of methyltrioctylammonium chloride and 13.16 ml (116 mmol) of tert-butyl mercaptan are added. After from 30 to 40 minutes, about 400 ml of water and about 400 ml of ethyl acetate are added, the mixture is extracted by shaking, the organic phase is separated off, the aqueous phase is extracted again with 200 ml of ethyl acetate, and the combined organic phases are washed with saturated NaCl solution. After drying with Na$_2$SO$_4$ or MgSO$_4$, the organic solution is concentrated by evaporation in vacuo and the residue is taken up in about 300 ml of tert-butyl methyl ether. Following filtration, the etherial solution is concentrated. The residue is brought to crystallization using n-heptane/ethyl acetate or n-heptane/tert-BuOMe. After complete crystallization the yield is 26.08–26.80 g (72–74%).

$^1$H-NMR (200 MHz, CDCl$_3$): σ=0.92 (d; 3H, CHC$\underline{H}_3$); 1.35 (s; 9H, C(CH$_3$)$_3$); 2.8–2.9 (m; 2H, CH$_2$CH$_2$); 3.2–3.3 (m; 2H, CH$_2$CH$_2$); 4.78 (quint; 1H, CHC$\underline{H}$CH$_3$); 5.68 (d; 1H, CHC$\underline{H}$Ph); 7.25–7.50 (m; 5H, Ph). m.p.: 68°–70° C.

EXAMPLE 5

Synthesis of Compound VIIIa Where R$^1$=C(CH$_3$)$_3$, R$^3$=Me, R$^5$=Ph 1.8 g (about 45 mmol) of NaH (60% pure) are washed with petroleum ether, and then 50 ml of THF are added. 5 g (28.2 mmol) of the oxazolidinone of the formula IIa where R$^3$=Me, R$^5$=Ph, are then dissolved in 20 ml of THF and this solution is added dropwise to the NaH/THF mixture. After stirring for one hour at room temperature the solution is cooled to –20° C., 2.35 ml (29.03 mmol) of acryloyl chloride are slowly added, and the mixture is stirred for a further 5 minutes.

18 ml of water are subsequently added, the mixture is warmed to room temperature, a pH of 10 is established, and 75 mg of tetra-n-butylammonium hydrogen sulfate are added and 2.87 ml (25.45 mmol) of tert-butyl mercaptan are added. After stirring for 2 hours at room temperature, 300 ml of water and 250 ml of ethyl acetate are added. Following extraction and drying with Na$_2$SO$_4$ the organic solution is concentrated in vacuo. The residue is stirred together with tert-butyl methyl ether. The fine precipitate which forms is filtered off and the etherial solution is concentrated to dryness by evaporation. Filtration over 10–15 g of silica gel (in CH$_2$Cl$_2$) and recrystallization from petroleum ether give 5.8–6.0 g (64–66%) of the pure Michael adduct of the formula VIIIa where R$^1$=C(CH$_3$)$_3$, R$^3$=Me, R$^5$=Ph.

$^1$H-NMR (200 MHz, CDCl$_3$): σ=0.92 (d; 3H, CHC$\underline{H}_3$); 1.35 (s; 9H, C (CH$_3$)$_3$); 2.8–2.9 (m; 2H, CH$_2$CH$_2$); 3.2–3.3 (m; 2H, CH$_2$CH$_2$); 4.78 (quint; 1H, CHC$\underline{H}$CH$_3$); 5.68 (d; 1H, CHC$\underline{H}$Ph); 7.25–7.50 (m; 5H, Ph). m.p.: 73°–75° C.

EXAMPLE 6

Synthesis of Compound VIIIb Where R$^1$=C(CH$_3$)$_3$, R$^4$=Me, R$^6$=Ph 0.676 g (16.92 mmol) of NaH (60%) are placed together with 25 ml of THF (dry). A solution of 2.5 g (14.1 mmol) of the oxazolidinone of the formula IIb where R$^4$=Me, R$^6$=Ph, in 10 ml of THF (dry) is added dropwise thereto at room temperature. After stirring for 1 h at room temperature, the mixture is cooled to –60° C. and 1.19 ml (14.8 mmol) of acryloyl chloride are slowly added dropwise. After about 10 minutes the reaction has ended. A previously prepared mixture of 2.0 ml (18.33 mmol) of t-butyl mercaptan and 19.2 ml (21.15 mmol) of a 1.1 molar solution of tetra-n-butylammonium fluoride in THF is then added dropwise. After 2 h at –60° C., 150 ml of water and 150 ml of ethyl acetate are added, the mixture is extracted by shaking, the organic phase is dried with MgSO$_4$ and the solvent is removed in vacuo. The residue is dissolved in tert-butyl methyl ether, the fine precipitate formed is filtered off with suction over a clarifying layer and discarded, and the etherial phase is concentrated in vacuo. The residue slowly solidifies. Recrystallization or filtration over a little silica gel (in CH$_2$Cl$_2$) gives 3.4 g (75%) of the desired Michael adduct of the formula VIIIb where R$^1$=C(CH$_3$)$_3$.

$^1$H-NMR (200 MHz, CDCl$_3$): σ=0.92 (d; 3H, CHC$\underline{H}_3$); 1.35 (s; 9H, C (CH$_3$)$_3$); 2.8–2.9 (m; 2H, CH$_2$CH$_2$); 3.2–3.3 (m; 2H, CH$_2$CH$_2$); 4.78 (quint; 1H, CHC$\underline{H}$CH$_3$); 5.68 (d; 1H, CHC$\underline{H}$Ph); 7.25–7.50 (m; 5H, Ph). m.p.: 69°–73° C.

EXAMPLE 7

Synthesis of Compound VIIIb Where R$^1$=C(CH$_3$)$_3$, R$^4$=Me, R$^6$=Ph 2.82 g (70.5 mmol) of NaH (60% pure) are washed with petroleum ether. 50 ml of dried tetrahydrofuran are then added, and a solution of 5 g (28.2 mmol) of the oxazolidinone of the formula IIb where $R^4$=Me, $R^6$=Ph, in 20 ml of THF is then added dropwise with stirring at room temperature. After stirring for one hour at room temperature, the mixture is cooled to −60° C. and 2.35 ml (29 mmol) of acryloyl chloride are slowly added, and the mixture is stirred for a further 10 minutes. 3.49 ml (31 mmol) of tert-butyl mercaptan are then added thereto at −60° C. After about 1.0–1.5 hours the reaction mixture is slowly added to 100 ml of saturated ammonium chloride solution. After it has warmed to room temperature, 200 ml of water and 300 ml of ethyl acetate are added. The mixture is extracted by shaking, the organic phase is separated off and dried with $MgSO_4$, and the solution is concentrated in vacuo. Tert-butyl methyl ether is added to the residue which remains, the turbidity is removed by filtration and the clear etherial solution is subsequently concentrated by evaporation. The residue crystallizes under cold conditions. Filtration over a little silica gel and recrystallization from n-heptane give 5.89 g (65%) of the desired compound VIIIb where $R^1$=$C(CH_3)_3$, $R^4$=Me, $R^6$=Ph.

$^1$H-NMR (200 MHz, $CDCl_3$): σ=0.92 (d; 3H, CHC$\underline{H}_3$); 1.35 (s; 9H, $C(CH_3)_3$); 2.8–2.9 (m; 2H, $CH_2CH_2$); 3.2–3.3 (m; 2H, $CH_2CH_2$); 4.78 (quint; 1H, CHC$\underline{H}CH_3$); 5.68 (d; 1H, CHC$\underline{H}$Ph); 7.25–7.50 (m; 5H, Ph). m.p.: 73°–75° C.

EXAMPLE 8

Synthesis of Compound (S)-XII where $R^1$=$C(CH_3)_3$ and $R^2$=1-Naphthyl 0.59 ml (4.2 mmol) of diisopropylamine are placed in 7 ml of THF. 2.5 ml (4.04 mmol) of BuLi (1.6M in hexane) are added dropwise at −60° C. The mixture is stirred at −60° C. for 10 minutes and then a solution of 1 g (3.11 mmol) of the compound of the formula VIIIa where $R^1$=tBu, $R^3$=Me, $R^5$=Ph in 3 ml of THF is added dropwise. Stirring is continued for 20 minutes and then a solution of 1.37 g (6.22 mmol) of 1-bromomethylnaphthalene in 3 ml of THF is added dropwise. The mixture is stirred for 5 minutes at −60° C. The temperature is subsequently allowed to rise to −10° C. over the course of 15 minutes by removing the cooling bath. After 40–60 minutes no more starting material is present, and 0.40 g (9.5 mmol) of $LiOH.H_2O$ and 1.0 ml (12 mmol) of $H_2O_2$ (35% strength) in 1 ml of $H_2O$ are added. The mixture is stirred for about 30 minutes at room temperature, the THF is concentrated by evaporation in vacuo, and the remaining reaction mixture is extracted with $CH_2Cl_2$. The aqueous phase is then acidified to pH=1 and is extracted thoroughly with ethyl acetate. The organic phase is dried with $Na_2SO_4$ and concentrated. 594 mg (60%) of the desired product are obtained.

$^1$H-NMR (200 MHz, $d_6$-DMSO): σ=1.10, 1.15 (s; 9H, SC($\underline{CH}_3)_3$); 2.70–3.70 (m; 5H, CH and $CH_2$); 7.1–8.2 (m; 7H, aromat.); 12.6 (br; 1H, COOH).

EXAMPLE 9

Conversion of the Alkylation Product of the Formula Xb Where $R^4$=Me, $R^6$=Ph, $R^1$=tBu into the (2R)-Sulfoxylcarboxylic Acid of the Formula XII Where $R^1$=$C(CH_3)_3$ and $R^2$=1-Naphthyl 200 mg (0.43 mmol) of the compound Xb where $R^4$=Me, $R^6$=Ph, $R^1$=tBu, $R^2$=1-naphthyl are dissolved in 2 ml of THF, and 0.11 ml (1.3 mmol) of $H_2O_2$ (35% pure) and 55 mg (1.3 mmol) of $LiOH.H_2O$ in 1 ml of water are added, and the mixture is stirred at room temperature. The reaction has ended after 30–40 minutes. The THF phase is separated off and then the reaction mixture is extracted with $CH_2Cl_2$ (recovery of the chiral auxiliary), and then the aqueous phase is acidified (pH=1) and the desired carboxylic acid is extracted with ethyl acetate. Drying ($Na_2SO_4$) and concentration in vacuo give 126 mg (92%) of the desired (2R)-sulfonylcarboxylic acid XII.

MS (70 eV): m/z (%)=319.2 (100, $M^{\oplus}$+1); 262.2 (25, M—$C_4H_8$).

EXAMPLE 10

Oxidation of the (2S)-Sulfoxide of the Formula XII Where $R^1$=$C(CH_3)_3$, $R^2$=Naphthyl to Give the (2S)-Sulfone of the Formula I ($R^1$=$C(CH_3)_3$, $R^2$=naphthyl)

500 mg (1.57 mmol) of (S)-sulfoxide XII (where $R^1$=$C(CH_3)_3$ and $R^2$=naphthyl) are dissolved in 1 ml of $CH_2Cl_2$.0.3 ml of glacial acetic acid, 0.52 ml of $H_2O_2$ and 0.16 g of polyphosphoric acid are added in succession. The reaction has ended after stirring for 2 h. Water is added to the reaction mixture and the phases are separated. The organic phase is washed twice with water, dried ($Na_2SO_4$) and concentrated on a rotary evaporator. 444 mg (84.7%) of the desired compound I in the (S) configuration are obtained.

$^1$H-NMR (270 MHz, $d_6$-DMSO) σ=1.25 (s; 9H, $O_2SC(CH_3)_3$); 3.1–3.65 (m; 5H, $CH_2$ and CH); 7.35–8.2 (m; 7H, aromat.); 12.55 (br.; 1H, COOH). MS (70 eV):m/z (%)=334 (100, $M^{\oplus}$).

EXAMPLE 11

Oxidation of the (2S)-Sulfoxide of the Formula XII Where $R^1$=$C(CH_3)_3$ to Give the (2S)-Sulfone of the Formula I ($R^1$=$C(CH_3)_3$), $R^2$=Phenyl)

790 mg (5 mmol) of $KMnO_4$ in 20 ml of water are added dropwise at room temperature to an aqueous solution (10 ml) of 1.34 g (5 mmol) of the mentioned (S)-sulfoxide formula XII and 300–500 mg of $K_2CO_3$. After the reaction has ended (monitoring by TLC) precipitated manganese dioxide was filtered off, the aqueous solution is acidified and the desired sulfone is extracted with ethyl acetate. Drying ($Na_2SO_4$) and concentration of the organic solution in vacuo give 1.25–1.35 g (88–95%) of the desired compound I where $R^1$=t-Bu, and $R^2$=phenyl, in the (S) configuration.

$^1$HNMR (200 MHz, $CDCl_3$) σ=1.3 (s; 9H, $O_2S$ $C(CH_3)_3$); 2.9–3.6 (m; 5H, $CH_2$ n. CH); 7.15–7.35 (m; 5H, Ph). MS (70 eV): m/z=284 ($M^{\oplus}$)

EXAMPLE 12

Oxidation of the (2R)-Sulfoxide of the Formula XII Where $R^1$=$C(CH_3)_3$, $R^2$=Phenyl to Give the (2R)-Sulfone of the Formula I ($R^1$=tBu, $R^2$=Phenyl)

670 mg (2.5 mmol) of the (R)-sulfoxide of the formula XII are placed in 5–10 ml of t-butyl methyl ether and 2–5 ml of water, and 2.5 g of Oxone in 10 ml of water is added dropwise at 0° C. The mixture is subsequently stirred at room temperature. After the reaction has taken place (monitoring by TLC) and the reaction mixture has been acidified the phases are separated. The aqueous phase is extracted twice with ethyl acetate and the combined organic phases are dried with $MgSO_4$. 682 mg (96%) of the desired sulfone of the formula I where $R^1 = C(CH_3)_3$ and $R^2$=phenyl are obtained in the (R) configuration.

$^1$H-NMR (200 MHz, CDCl$_3$) σ=1.3 (s; 9H, O$_2$S C (CH$_3$)$_3$); 2.9–3.6 (m; 5H, CH$_2$ n. CH); 7.15–7.35 (m; 5H, Ph). MS (70 eV): m/z=284 (M$^⊕$)

EXAMPLE 13

Synthesis of (4S,5R)-3-(1-Oxo-3-chloropropyl)-4-methyl-5-phenyl-2-oxazolidinone (Compound of the Formula VIb Where $R^4$=Methyl, $R^6$=Phenyl, X=Cl)

0.52 g (12 mmol) of NaH (60%) are placed in 2 ml of THF. A solution of 1.32 g (7.45 mmol) of (4S,5R)-4-methyl-5-phenyl-2-oxazolidinone in 13 ml of THF is added dropwise thereto with stirring. After stirring for 30–40 minutes at room temperature, 1.23 g (9.7 mmol) of 3-chloropropionyl chloride are slowly added dropwise thereto at −60° C. and the mixture is then stirred for about 30 min. at −60° C. 10 to 15 ml of citric acid/water are then added at from −60° to −40° C., the reaction temperature is allowed to rise slowly to 25° C., the reaction mixture is extracted by shaking with ethyl acetate, and the organic phase is dried with MgSO$_4$ and concentrated in vacuo. Crystallization gives 1.3–1.4 g (65–70%) of the desired product.

$^1$H-NMR (200 MHz, CDCl$_3$): σ=0.92 (d; 1H, CHC$\underline{H}_3$); 3.4–3.5 (m; 2H, C$\underline{H}_2$CH$_2$); 3.8–3.9 (m; 2H, CH$_2$C$\underline{H}_2$); 4.80 (quint; 1H, CHC$\underline{H}$CH$_3$); 5.70 (d; 1H, CHC$\underline{H}$Ph); 7.2–7.5 (m; 5H, Ph).

EXAMPLE 14

Precipitation of Compounds of the Formula I As Cyclohexylammonium Salt 21 g of I are dissolved in 200 ml of acetone, and 6 g of cyclohexylamine are added. After dilution with 100 ml of acetone the solid product is filtered off with suction. 20.4 g of the cyclohexylammonium salt of I are obtained.

EXAMPLE 15

Liberation of Compounds of the Formula I from the Cyclohexylammonium Salt 15 g of the salt are admixed with 100 ml of ethyl acetate and 100 ml of 2N HCl, and the mixture is extracted by shaking. The organic phase is washed with 100 ml of saturated NaCl solution, dried with Na$_2$SO$_4$ and concentrated. 12 g of the free acid I are obtained.

EXAMPLE 16

Differentiation of (S)-I and (R)-I (S)-I and/or (R)-I, dissolved in methylene chloride, are cooled to 0° C., and an excess of triethylamine, (S)-phenylalaninol and propanephosphonic anhydride is added, and then the mixture is stirred for about 1 h at room temperature. The diastereomeric amides can be differentiated both by HPLC and by TLC: e.g. for I where $R^1$=tBu, $R^2$=naphthyl:

(S)-I-(S)-phenylalaninolamide Rf (tBuOMe) 0.60

(R)-I-(S)-phenylalaninolamide Rf (tBuOMe) 0.32

EXAMPLE 17

Synthesis of Compound VIIIa Where $R^1$=C(CH$_3$)$_3$, $R^3$=Me, $R^5$=Ph 2 ml of abs. THF are added to 0.515 g (11.8 mmol) of NaH (about 60%). Then 1.32 g (7.45 mmol) of the oxazolidinone IIa where $R^3$=Me, $R^5$=Ph are added and the mixture is stirred for 0.5–1.0 h at room temperature. It is cooled to −60° C. and then 0.72 ml (7.45 mmol) of 3-chloropropionyl chloride is slowly added.

The reaction mixture is stirred for 30–45 min. at −60° C., and then a mixture of 20 mg of tetrabutylammonium hydrogen sulfate, 15 ml of water and 0.86 ml (7.66 mmol) of tert-butyl mercaptan is added. The reaction mixture is allowed to warm up slowly to room temperature, a pH of 9–11 is established and the mixture is stirred for 1 to 2 hours at room temperature.

Subsequently, following the addition of from 50 to 100 ml of water, the mixture is extracted with ethyl acetate, and the organic phase is dried and concentrated; crude product: 2.3 g.

Filtration over about 6 g of silica gel and crystallization from cyclohexane give 1.7 g (73%) of the desired compound VIII where $R^1$=C(CH$_3$)$_3$.

Spectroscopic data: $^1$H-NMR (200 MHz, CDCl$_3$): σ=0.92 (d; 3H, CHC$\underline{H}_3$); 1.35 (s; 9H, C (CH$_3$)$_3$); 2.8–2.9 (m; 2H, CH$_2$CH$_2$); 3.2–3.3 (m; 2H, CH$_2$CH$_2$); 4.78 (quint; 1H, CHC $\underline{H}$CH$_3$); 5.68 (d; 1H, CHC$\underline{H}$Ph); 7.25–7.50 (m; 5H, Ph).

EXAMPLE 18

Synthesis of Compound VIIIa Where $R^1$=C(CH$_3$)$_3$, $R^3$=Me, $R^5$=Ph 2.6 g (59 mmol) of NaH (60% dispersion) and 6.6 g (37.25 mmol) of the oxazolidinone of the formula IIa where $R^3$=Me, $R^5$=Ph are stirred in 10 ml of abs. THF for one hour at room temperature. The mixture is then cooled to −60° C., 3.58 ml (37.25 mmol) of chloropropionyl chloride are added dropwise, and the mixture is stirred for 30–45 min. at −60° C. Following the addition of 1.3 g (6.8 mmol) of dry citric acid, the mixture is stirred for 5–15 min at 60° C., then 50 ml of water are slowly added, the temperature is raised to from −10° to 0° C., 100 mg of nBu$_4$NHSO$_4$ are added, and a pH of 9–10 is established with 5N NaOH. Following the addition of 4.31 ml (38.6 mmol) of tert-butyl mercaptan, the mixture is stirred for 2 h at room temperature. In order to work up the reaction, 200 ml of ethyl acetate and 200 ml of semisaturated citric acid solution are added, the mixture is extracted with shaking, and the organic phase is washed with water, dried with MgSO$_4$ and concentrated in vacuo;

crude yield 12 g. Filtration over about 25 g of silica gel (CH$_2$Cl$_2$) and extraction by stirring with hexane or pentane give 7.8 g (65%) of the desired product.

m.p.: 73°–75° C.

We claim:

1. A process for the stereoselective preparation of a compound of the formula I

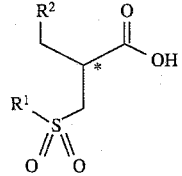

in which $R^1$ is $C_1$–$C_6$-alkyl, $C_3$–$C_6$-cycloalkyl, $(C_6$–$C_{12})$-aryl-$(C_1$–$C_4)$-alkyl or $C_6$–$C_{12}$-aryl or -heteroaryl or -heterocycloalkyl which is unsubstituted or substituted by 1, 2 or 3 identical or different hydroxyl, methoxy or trialkylsilyloxy groups; and $R^2$ is $C_6$–$C_{12}$-aryl which is unsubstituted or substituted by 1, 2 or 3 identical or different methoxy, halogen, cyano, methyl, trifluoromethyl, isopropyl or nitro groups;

is $C_3$–$C_9$-heteroaryl which is unsubstituted or substituted by 1, 2 or 3 identical or different methoxy, halogen, cyano, methyl, trifluoromethyl, isopropyl or nitro groups; or is $C_1$–$C_{10}$-alkyl, alkenyl or alkynyl which is unsubstituted or substituted by 1, 2 or 3 identical or different methoxy, halogen, cyano, methyl, trifluoromethyl, isopropyl or nitro groups and the compounds of the formula I may be present in the R or S form, which process comprises reacting a compound of the formula IIa or IIb or IIIa or IIIb, respectively, (chiral auxiliary), in which Y is =O or S,

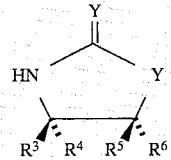

| | |
|---|---|
| $R^3=C_1$–$C_4$-alkyl, $R^5=C_6$–$C_{10}$-aryl, $R^4=R^6=H$, | IIa |
| $R^4=C_1$–$C_4$-alkyl, $R^6=C_6$–$C_{10}$-aryl, $R^3=R^5=H$, | IIb |
| $R^3=C_1$–$C_4$-alkyl, $C_1$–$C_2$-alkyl-$C_6$–$C_{12}$-aryl, $R^4=R^5=R^6=H$, | IIIa |
| $R^4=C_1$–$C_4$-alkyl, $C_1$–$C_2$-alkyl-$C_6$–$C_{12}$-aryl, $R^3=R^5=R^6=H$, | |

$a_1$) with acrylic acid or with a derivative of acrylic acid, to form a compound of the formula IVa or IVb or Va or Vb, respectively, in which Y is =O or S,

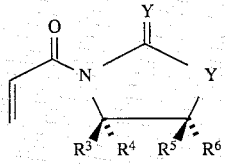

| | |
|---|---|
| $R^3=C_1$–$C_4$-alkyl, $R^5=C_6$–$C_{10}$-aryl, $R^4=R^6=H$, | IVa |
| $R^4=C_1$–$C_4$-alkyl, $R^6=C_6$–$C_{10}$-aryl, $R^3=R^5=H$, | IVb |
| $R^3=C_1$–$C_4$-alkyl, $C_1$–$C_2$-alkyl-$C_6$–$C_{12}$-aryl, $R^4=R^5=R^6=H$, | Va |
| $R^4=C_1$–$C_4$-alkyl, $C_1$–$C_2$-alkyl-$C_6$–$C_{12}$-aryl, $R^3=R^5=R^6=H$, | Vb | or $a_2$) with propionic acid or a propionic acid derivative which are in turn substituted in position $C_3$ by a radical X=Cl, Br, OTs, OMs, to form a compound of the formula VIa or VIb or VIIa or VIIb, respectively, in which X and Y are as defined above,

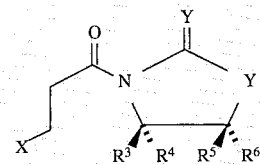

| | |
|---|---|
| $R^3=C_1$–$C_4$-alkyl, $R^5=C_6$–$C_{10}$-aryl, $R^4=R^6=H$, | VIa |
| $R^4=C_1$–$C_4$-alkyl, $R^6=C_6$–$C_{10}$-aryl, $R^3=R^5=H$, | VIb |
| $R^3=C_1$–$C_4$-alkyl, $C_1$–$C_2$-alkyl-$C_6$–$C_{12}$-aryl, $R^4=R^5=R^6=H$, | VIIa |
| $R^4=C_1$–$C_4$-alkyl, $C_1$–$C_2$-alkyl-$C_6$–$C_{12}$-aryl, $R^3=R^5=R^6=H$, | VIIb | b) reacting the compound of the formula IVa, IVb, Va, Vb, VIa, VIb, VIIa or VIIb obtained according to $a_1$) or $a_2$), directly or after isolation in a nonaqueous medium or in the presence of a phase-transfer catalyst in an aqueous two-phase system, with a mercaptan of the formula $R^1SH$, in which $R^1$ is as defined above, into the corresponding compound of the formula VIIIa or VIIIb or IXa or IXb, respectively, in which $R^1$ and Y are as defined above,

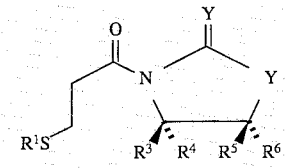

| | |
|---|---|
| $R^3=C_1$–$C_4$-alkyl, $R^5=C_6$–$C_{10}$-aryl, $R^4=R^6=H$, | VIIIa |
| $R^4=C_1$–$C_4$-alkyl, $R^6=C_6$–$C_{10}$-aryl, $R^3=R^5=H$, | VIIIb |
| $R^3=C_1$–$C_4$-alkyl, $C_1$–$C_2$-alkyl-$C_6$–$C_{12}$-aryl, $R^4=R^5=R^6=H$, | IXa |
| $R^4=C_1$–$C_4$-alkyl, $C_1$–$C_2$-alkyl-$C_6$–$C_{12}$-aryl, $R^3=R^5=R^6=H$, | IXb | or $a_3$) converting a compound of the formula IIa or IIb or IIIa or IIIb, respectively, in the presence of a quantity of a base which is sufficient for the deprotonation of the oxazolidinone and of the mercaptan $R^1SH$, in which $R^1$ is as defined above, into a compound of the formula VIIIa or VIIIb or IXa or IXb, respectively, by reaction with acryloyl or propionyl halides or their respective mixed anhydrides and further reaction of the reaction product with the mercaptan in one step, c) then converting the compound obtained according to b) or $a_3$) into the corresponding compound of the formula Xa, Xb, XIa or XIb by stereoselective alkylation,

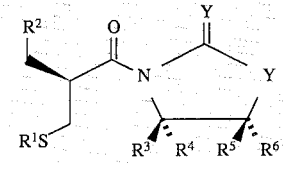

| | |
|---|---|
| $R^3=C_1$–$C_4$-alkyl, $R^4=R^6=H$, $R^5=C_6$–$C_{12}$-aryl, | Xa |
| $R^3=C_1$–$C_4$-alkyl, $C_1$–$C_2$-alkyl-$C_6$–$C_{12}$-aryl, $R^4=R^5=R^6=H$, | XIa |

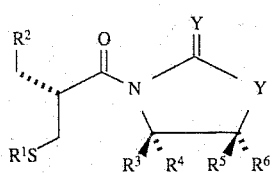

$R^4 = C_1-C_4\text{-alkyl, } R^6 = C_6-C_{12}\text{-aryl, } R^3 = R^5 = H,$  Xb $R^4 = C_1-C_4\text{-alkyl, } C_1-C_2\text{-alkyl-}C_6-C_{12}\text{-aryl, } R^3 = R^5 = R^6 = H,$  XIb in which Y, $R^1$ and $R^2$ are as defined above,
d) then converting the compound obtained in this way by reaction with $H_2O_2$ in alkaline solution, into compounds of the formula XII which may be present in the R or S form,

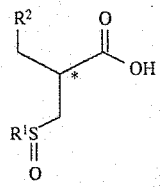   XII and
e) then converting the compound obtained in this way, by further oxidation, into the corresponding compound of the formula I.

2. The process as claimed in claim 1, wherein
$R^1$ is $C_1-C_4$-alkyl, $C_5-C_6$-cycloalkyl, $(C_6-C_{12})$-aryl-$(C_1-C_3)$-alkyl or $C_6-C_{12}$-aryl or -heteroaryl which is unsubstituted or substituted by a hydroxyl, methoxy or trialkylsilyloxy group; and
$R^2$ is $C_6-C_{12}$-aryl which is unsubstituted or substituted by a methoxy, halogen, methyl, trifluoromethyl or isopropyl group;

is $C_3-C_6$-heteroaryl which is unsubstituted or substituted by a methoxy, halogen, methyl, trifluoromethyl or isopropyl group, or
is $C_1-C_4$-alkyl, -alkenyl or -alkynyl.

3. The process as claimed in claims 1 or 2, wherein
$R^1$ is $C_1-C_4$-alkyl, $(C_6-C_{12})$-aryl-$(C_1-C_3)$-alkyl or $C_6-C_{12}$-aryl, and
$R^2$ is $=C_6-C_{12}$-aryl, $C_3-C_6$-heteroaryl or $C_1-C_4$-alkyl, -alkenyl or -alkynyl.

4. The process as claimed in claim 1, wherein a compound of the formula IIa or IIb or IIIa or IIIb, respectively, in which

| | |
|---|---|
| $R^3$=Me, $R^5$=Ph, $R^4$=$R^6$=H | IIa |
| $R^4$=Me, $R^6$=Ph, $R^3$=$R^5$=H | IIb |
| $R^3$=CH(CH$_3$)$_2$, $R^4$=$R^5$=$R^6$=H | IIIa |
| $R^4$=CH(CH$_3$)$_2$, $R^3$=$R^5$=$R^6$=H | IIIb | and Y is =O is employed.

5. The process as claimed in claim 1, wherein the compound of the formula IIa or IIb or IIIa or IIIb, respectively, is converted in accordance with $a_3$) in one step directly into a compound of the formula VIIIa or VIIIb or IXa or IXb.

6. The process as claimed in claim 1, wherein the alkylation of the compound of the formula VIIIa, VIIIb, IXa or IXb, the subsequent elimination of the chiral auxiliary and the oxidation to give the compounds of the formula XII or I, respectively, is carried out without isolating the intermediates.

7. The process as claimed in claim 1, wherein in step (d) the compound is reacted with LiOH/$H_2O_2$.

* * * * *